United States Patent [19]

Logan et al.

[11] 4,282,164

[45] Aug. 4, 1981

[54] FRACTIONATION OF ALKYLCARBOXYLATE MIXTURES

[75] Inventors: Ted J. Logan; Richard M. King, both of Cincinnati, Ohio

[73] Assignee: The Procter & Gamble Company, Cincinnati, Ohio

[21] Appl. No.: 108,988

[22] Filed: Jan. 2, 1980

[51] Int. Cl.[3] .......................... C09F 5/10; C11B 3/00

[52] U.S. Cl. .......................... 260/428.5; 260/428; 260/410.9 R; 560/218

[58] Field of Search .......................... 260/428.5; 560/218

[56] References Cited

U.S. PATENT DOCUMENTS

| | | | |
|---|---|---|---|
| 852,441 | 5/1907 | Lockwood | 260/428.5 |
| 2,197,861 | 4/1940 | Hyman | 260/428.5 |
| 2,288,441 | 6/1942 | Ewring | 260/428.5 |
| 2,314,621 | 3/1943 | Kelley | 260/425 |
| 2,509,509 | 5/1950 | Leaders | 260/428.5 |
| 2,577,079 | 12/1951 | Gee | 260/428.5 |
| 2,985,589 | 5/1961 | Broughton | 210/34 |
| 4,048,205 | 9/1977 | Neuzil | 260/428.5 X |
| 4,049,688 | 9/1977 | Neuzil | 260/428.5 X |
| 4,189,442 | 2/1980 | Lubsen et al. | 260/428.5 |
| 4,213,913 | 7/1980 | de Rosset | 260/428.5 |

FOREIGN PATENT DOCUMENTS

| | | | |
|---|---|---|---|
| 1476511 | 6/1977 | United Kingdom | 260/428.5 |

OTHER PUBLICATIONS

Lam et al., J. Chrom. Sci. 15, pp. 234–238, Jul. 1977.
Breck D., *Zeolite Molecular Sieves*, New York, (1974).
Chem. and Ind. 24, pp. 150–151 and 1049–1050, (1962).
JAOCS, 41, pp. 403–406, Jun. 1964.

*Primary Examiner*—John F. Niebling
*Attorney, Agent, or Firm*—Ronald L. Hemingway; Richard C. Witte

[57] ABSTRACT

Alkyl fatty carboxylate mixture is separated according to degree of unsaturation utilizing selected surface aluminated silica gel adsorbent and selected solvent(s).

18 Claims, No Drawings

FRACTIONATION OF ALKYLCARBOXYLATE MIXTURES

TECHNICAL FIELD

The field of this invention is the separation of alkyl fatty ($C_6$–$C_{26}$) carboxylate mixture to obtain fractions of lesser degree of unsaturation and of higher degree of unsaturation (i.e. separating such mixture according to degree of unsaturation). The separated fractions are useful, for example, as chemical intermediates in the manufacture of fatty chemical derivatives.

Fractional distillation is the most common method now being used commercially to separate alkyl fatty carboxylate mixtures. This unit operation separates primarily on the basis of chain length. While it may provide very slight separation on the basis of unsaturation with conventional equipment, adequate separation would require a very large number of theoretical stages.

Fractional solvent crystallization, which is used to separate fatty acids on the basis of unsaturation, is not economic for alkyl fatty carboxylates. Temperatures of minus 50° F. to minus 70° F. and lower would have to be used, the crystals would be very fragile, and there would be a mutual solubility between unsaturate components; this provides a very expensive process for a substantially incomplete separation.

Urea adduction is another uneconomic process for separating alkyl fatty carboxylates. This consists, for example, of admixing the mixture to be separated with urea and acetone and cooling whereby the urea forms a crystal cage around the highest melting point component (usually the saturates). Recovery of separated fraction from the adduct is difficult. Moreover, this process is not as effective for separating one unsaturate from another. Furthermore, this process is difficult to adapt to continuous operation.

BACKGROUND ART

Neuzil et al U.S. Pat. No. 4,048,205 and Neuzil et al U.S. Pat. No. 4,049,688 and Logan et al U.S. Pat. No. 4,210,594 disclose the fractionation of alkyl fatty carboxylate mixtures using synthetic crystalline aluminosilicates (zeolites). These crystalline aluminosilicate adsorbents typically contain up to about 25% amorphous aluminosilicate, e.g., clay. The process of the invention herein differs, for example, in the adsorbent which is advantageous over the crystalline adsorbents from the standpoints of versatility (in that, with the adsorbent herein, the same equipment and packing is advantageously used for separation of alkyl carboxylates and triglycerides—this is not true for crystalline zeolites) and flexibility (in that various ratios of surface-silicon atoms to aluminum atoms and various surface areas are readily available for the adsorbent herein—there is substantially less choice for crystalline zeolites).

Lubsen et al U.S. Pat. No. 4,189,442 issued Feb. 19, 1980 discloses the fractionation of alkyl fatty carboxylate mixtures utilizing macroreticular strong acid cation exchange resin adsorbents. The invention herein differs, for example, in utilizing an adsorbent different from that disclosed in U.S. Pat. No. 4,189,442 and advantageous over the adsorbent disclosed in Ser. No. 019,691 from the standpoints of flexibility, capacity, cost, and of being inorganic rather than organic in nature.

It is known on an analytical scale to separate alkyl fatty carboxylate mixtures utilizing silica gel treated with silver nitrate. See *Chemistry and Industry* 24, pp. 1049–50 (June 1962). The adsorbent there has the disadvantage of having a short life cycle in that the silver nitrate is leached out since it is not chemically attached. The adsorbent used herein has no such short life cycle problem.

British Pat. No. 1,476,511 (complete specification published June 16, 1977) which corresponds to German Pat. No. 2,335,890, assigned to Henkel, discloses using an aluminosilicate clay as an acidic catalyst to polymerize multiple unsaturated components of a mixture of esters of fatty acids and distilling to separate unpolymerized material from polymerized material. Such process has the disadvantage of producing unuseful polymerized material. The process of the instant invention is carried out without significant polymerization occurring.

Lam et al, "Silver Loaded Aluminosilicate As a Stationary Phase for the Liquid Chromatographic Separation of Unsaturated Compounds", *J. Chromatog. Sci.* 15 (7), 234–8 (1977) discloses the analytical (chromatographic) separation of bromophenacyl carboxylates on the basis of unsaturation utilizing silvered, surface aluminated silica gel adsorbents of microparticulate particle size (which particle size is not readily handled in a non-analytical commercial context and can result in significant loss due to suspension of particles in solvent). The process of the instant invention differs at least in the feedstock and the adsorbent particle size.

BROAD DESCRIPTION OF THE INVENTION

It is an object of this invention to provide a process for separating alkyl fatty carboxylates according to degree of unsaturation which does not require low uneconomic temperatures or difficult recovery of product and which can separate one unsaturate from another and which is readily operated on a continuous basis.

It is an object of this invention to provide a process for fractionating alkyl carboxylate mixtures on the basis of degree of unsaturation utilizing an adsorbent which is made from low cost and readily available materials, which is readily provided with selected characteristics (ready choice in ratio of surface-silicon atoms to aluminum atoms, silica gel surface area, and cation substituents and level thereof), which is not subject to a cation leaching problem (as is silver nitrate treated silica gel), which has a particle size appropriate for commercial processing (no significant handling or loss problems as with microparticulate particle sizes), which is advantageous over crystalline zeolite adsorbents from the standpoints of flexibility and versatility and which is advantageous over resin adsorbents from the standpoints of flexibility, capacity, cost, and of being inorganic in nature.

It is still a further object to provide a process which is carried out without significant polymerization occurring.

It is an object of one embodiment of the process herein to provide a process for obtaining products containing high percentages of a methyl ester, especially a particular unsaturated methyl ester such as methyl oleate or methyl linoleate, starting with readily available feedstocks.

These objects and other objects and advantages are readily obtained by the invention herein as described below.

The invention herein involves fractionating alkyl fatty ($C_6$–$C_{26}$) carboxylate mixture according to degree of unsaturation utilizing selected solvent(s) and selected surface aluminated silica gel adsorbent.

The feed (sometimes called feedstock) is a mixture of alkyl carboxylates with different degrees of unsaturation in the carbon chain in the carboxylic acid moiety (a mixture of alkyl carboxylate of higher degree of unsaturation with alkyl carboxylate of lesser degree of unsaturation) which is to be separated into fractions of higher degree of unsaturation and lesser degree of unsaturation. Alkyl carboxylates in the feed have alkyl containing one to four carbon atoms and carboxylic acid moiety with a carbon chain containing from 6 to 26 carbon atoms.

The feed is dissolved in particular solvent (the adsorption vehicle). The solution which is formed is contacted with particular surface aluminated silica gel adsorbent. Alkyl carboxylate of higher degree of unsaturation is selectively adsorbed on such adsorbent, and a fraction of the mixture which is enriched (compared to the feed) in content of alkyl carboxylate of lesser degree of unsaturation is left in solution in solvent.

Solution in solvent of the fraction which is enriched in content of alkyl carboxylate of lesser degree of unsaturation is removed from contact with the adsorbent which has selectively adsorbed alkyl carboxylate of higher degree of unsaturation; this solution is denoted a raffinate. Fraction enriched in content of alkyl carboxylate of lesser degree of unsaturation can readily be recovered from the raffinate as described later.

The adsorbent which has selectively adsorbed thereon alkyl carboxylate of higher degree of unsaturation is contacted with particular solvent (the desorbent) to cause desorption of adsorbed alkyl carboxylate and provide a solution in the solvent of fraction enriched (compared to the feed) in content of alkyl carboxylate of higher degree of unsaturation.

Solution in solvent of fraction enriched in content of alkyl carboxylate of higher degree of unsaturation is removed from contact with the adsorbent which has undergone desorption of alkyl carboxylate; this solution is denoted an extract. Fraction enriched in content of alkyl carboxylate of higher degree of unsaturation can be readily recovered from the extract as described later.

Preferred is a process where the solvent which is used to dissolve feed for selective adsorption (that is, the adsorption vehicle), and the solvent which is used as the vehicle for desorption (that is, the desorbent) have the same composition. Such process is conveniently referred to herein as a one solvent process. Preferably, such one solvent process is carried out continuously utilizing a simulated moving bed unit operation.

Less preferred is a process where the solvent which is used as the dissolving phase during adsorption and the solvent which is used as the vehicle for desorption have different compositions. This process is conveniently referred to herein as a two solvent process.

In general, the solvent(s) utilized herein (whether in a one solvent process or in a two solvent process) is (are) characterized by a solubility parameter (on a 25° C. basis) ranging from about 7.0 to about 15.0, a solubility parameter dispersion component (on a 25° C. basis) ranging from about 7.0 to about 9.0, a solubility parameter polar component (on a 25° C. basis) ranging from 0 to about 6.0 and a solubility parameter hydrogen bonding component (on a 25° C. basis) ranging from 0 to about 11.5.

The surface aluminated silica gel adsorbent for the process herein is a synthetic amorphous aluminosilicate cation exchange material. It is homogeneous with respect to silicon atoms but not with respect to aluminum atoms; aluminum atoms are present essentially entirely at the surface of the adsorbent (i.e., they are associated with surface-silicon atoms) and are considered to be essentially completely in the form of aluminate moieties.

The adsorbent is derived from silica gel having a surface area of at least about 100 square meters per gram. The adsorbent is further characterized by a ratio of surface-silicon atoms to aluminum atoms ranging from about 3:1 to about 20:1, a moisture content less than about 10% by weight, and a particle size ranging from about 200 mesh to about 20 mesh.

The adsorbent has cation substituents selected from the group consisting of cation substituents capable of forming $\pi$ complexes and cation substituents not capable of forming $\pi$ complexes and combinations of these.

The adsorbent is formed by first treating particular silica gel with aluminate ion; then, if necessary, adjusting the cation content (e.g. by providing a selected level of cation substituents capable of forming $\pi$ complexes); and adjusting the moisture content. Particle size can also be adjusted.

The solvent(s) (that is, the adsorption vehicle and the desorbent, whether in a one solvent process or a two solvent process), the ratio of surface-silicon atoms to aluminum atoms in the adsorbent, and the level of cation substituents capable of forming $\pi$ complexes (which level can range from none at all up to 100% of exchange capacity) are selected to provide selectivity during adsorption and satisfactory desorption of adsorbed alkyl carboxylate.

Processing is carried out without significant polymerization of alkyl carboxylate occurring.

The invention herein contemplates one stage processing as well as processing in a plurality of stages. One stage processing is suitable for separating a mixture into two fractions. Multistage processing is suitable for separating a mixture into more than two fractions.

As used herein, the term "selectively" in the phrase "selectively adsorb" describes the ability of the adsorbent to preferentially adsorb a component or components. In practice, the component(s) which is (are) preferentially adsorbed, is (are) rarely ever the only component(s) adsorbed. For example, if the feed contains one part of a first component and one part of a second component, and 0.8 parts of the first component and 0.2 parts of the second component are adsorbed, the first component is selectively adsorbed.

The magnitude of the selective adsorption is expressed herein in terms of relative selectivity, that is, the ratio of two components in the adsorbed phase (extract) divided by the ratio of the same two components in the unadsorbed phase (raffinate). In other words, relative selectivity as used herein is defined by the following equation:

$$\text{Selectivity} = [\text{Concentration M}/\text{Concentration N}]_A / [\text{Concentration M}/\text{Concentration N}]_U$$

where M and N are two components of the feed represented in volume or weight percent and the subscripts A and U represent the adsorbed and unadsorbed phases respectively. When the selectivity is 1.0, there is no preferential adsorption of one component over the other. A selectivity larger than 1.0 indicates preferential adsorption of component M; in other words, the extract phase is enriched in M and the raffinate phase is enriched in N. The farther removed the selectivity is from 1.0, the more complete the separation.

The amount selectively adsorbed per unit volume of adsorbent in a batch equilibrium test (mixing of feed dissolved in solvent with adsorbent for up to one hour or until no further change in the chemical composition of the liquid phase occurs) is the static capacity of the adsorbent. An advantage in static capacity indicates a potential advantage in dynamic capacity. Dynamic capacity is the production rate in continous operation in apparatus of predetermined size to obtain predetermined purity product(s). The term "capacity" as used herein means both static and dynamic capacity unless the context indicates otherwise.

Separating "according to degree of unsaturation" is used herein to mean separating an alkyl carboxylate mixture (containing alkyl carboxylates with different degrees of unsaturation) to provide first fraction enriched in alkyl carboxylate of higher degree of unsaturation and second fraction enriched in alkyl carboxylate of lesser degree of unsaturation. The more double bonds in the carbon chain in the carboxylic acid moiety, the higher is the degree of unsaturation. Thus, ester of triunsaturated (three double bonds in the carbon chain in the carboxylic acid moiety) fatty acid has a higher degree of unsaturation than ester of diunsaturated (two double bonds in the carbon chain in the carboxylic acid moiety) fatty acid which in turn has a higher degree of unsaturation than ester of monounsaturated (one double bond in the carbon chain in the carboxylic acid moiety) fatty acid which in turn has a higher degree of unsaturation than ester of saturated (no double bonds in the carbon chain in the carboxylic acid moiety) fatty acid.

The meaning of the terms "alkyl carboxylate of higher degree of unsaturation" and "alkyl carboxylate of lesser degree of unsaturation" as used herein depends on the context, that is the particular separation to which the invention is being applied. The alkyl carboxylate of higher degree of unsaturation can include more than one alkyl carboxylate and can include alkyl carboxylates with different degrees of unsaturation. Likewise the alkyl carboxylate of lesser degree of unsaturation can include more than one alkyl carboxylate and can include alkyl carboxylates with different degrees of unsaturation. The alkyl carboxylate of higher degree of unsaturation has to include the alkyl carboxylate of highest degree of unsaturation, and the alkyl carboxylate of lesser degree of unsaturation has to include the alkyl carboxylate of lowest degree of unsaturation. The alkyl carboxylate of lesser degree of unsaturation includes ester of saturated fatty acid, if such is present in the mixture being separated. In a multistage process, the alkyl carboxylate of higher degree of unsaturation in one stage can be different from the alkyl carboxylate of higher degree of unsaturation in another stage and the alkyl carboxylate of lesser degree of unsaturation in one stage can be different from the alkyl carboxylate of lesser degree of unsaturation in another stage. For example, in a two stage process where the feed to the first stage comprises methyl linolenate, methyl linoleate, methyl oleate and methyl stearate and the feed to the second stage is fraction obtained on striping solvent from raffinate from the first stage, in the first stage the alkyl carboxylate of higher degree of unsaturation might be methyl linolenate and methyl linoleate and the alkyl carboxylate of lesser degree of unsaturation might be methyl oleate and methyl stearate, and in the second stage the alkyl carboxylate of higher degree of unsaturation might be methyl oleate and the alkyl carboxylate of lesser degree of unsaturation might be methyl stearate.

The terms "alkyl carboxylate" and "alkyl fatty carboxylate" are used interchangeably herein.

The term "solvent" as used herein refers both to solvent blends (i.e., solvents consisting of a plurality of constituents) and to pure compounds (i.e., solvents consisting of a single constituent) unless the context indicates otherwise.

The terms "solubility parameter", "solubility parameter dispersion component", "solubility parameter polar component" and "solubility parameter hydrogen bonding component" as used herein are defined by equations 6–10 at page 891 of Kirk-Othmer, *Encyclopedia of Chemical Technology,* 2nd Edition, Supplement Volume, published by Interscience Publishers (John Wiley & Sons) New York, 1971. Values herein for solubility parameter, solubility parameter dispersion component, solubility parameter polar component and solubility parameter hydrogen bonding component are for solvents at 25° C. (i.e., they are on a 25° C. basis). As on page 891, the symbols "$\delta$", "$\delta_D$", "$\delta_P$", and "$\delta_H$" are used herein to refer respectively to "solubility parameter", "solubility parameter dispersion component", "solubility parameter polar component", and "solubility parameter hydrogen bonding component". For many solvents the values for $\delta_D$, $\delta_P$, and $\delta_H$ are given in Table I which directly follows page 891 and the value for $\delta$ is calculated using equation (6) on page 891. For solvents consisting of a plurality of constituents, the values for "$\delta_D$", "$\delta_P$" and "$\delta_H$" are calculated by summing the corresponding values for the constituents multiplied by their volume fractions and the value for "$\delta$" is calculated using equation (6) on page 891.

The "surface area" of the silica gel is measured by the B.E.T. nitrogen adsorption technique described in Brunauer, Emmett and Teller, *J. Am. Chem. Soc.* 60, p. 309 (1938).

The term "surface-silicon atom" as used herein means a silicon atom attached to only three other silicon atoms by Si—O bonds.

Determination of the ratio of surface-silicon atoms to aluminum atoms in the surface aluminated silica gel adsorbent is readily carried out by determining the number of surface-silicon atoms assuming the presence of 8 silicon atoms per square nanometer of surface area (the figure of 8 silicon atoms per square nanometer of surface area is found, for example, in Iler, R. K. *The Colloid Chemistry of Silica and Silicates,* Cornell University Press, Ithaca, New York 1955, p. 58) of the silica gel from which the adsorbent is derived and determining the number of aluminum atoms, for example, utilizing elemental analysis, and calculating.

The term "cation substituents" means the exchangeable cations associated with the adsorbent. The "cation substituents capable of forming $\pi$ complexes" are cation substituents capable of attracting and holding unsaturated materials (the greater the degree of unsaturation, the greater the attracting and holding power) by formation of a particular kind of chemisorption bonding known as $\pi$ bonding. The "cation substituents not capable of forming $\pi$ complexes" do not have significant ability to form such chemisorption bonds. The formation of $\pi$ complexes is considered to involve two kinds of bonding: (1) overlap between occupied $\pi$ molecular orbital of an unsaturate and an unoccupied d orbital or dsp-hybrid orbital of a metal and (2) overlap between an unoccupied antibonding $\pi^*$ molecular orbital of the unsaturate and one of the occupied metal d or dsp-hybrid orbitals (sometimes referred to as "back bonding"). This $\pi$ complexing is described, for example, in *Chem. Revs.* 68, pp. 785-806 (1968).

The term "adsorbent surface area" as used hereinafter in defining silver substituents level is also measured by the B.E.T. nitrogen adsorption technique referred to above and is measured on the adsorbent after silvering and moisture adjustment.

The level of silver substituents is referred to hereinafter in terms of millimoles/100 square meters of adsorbent surface area. This is determined by determining the amount of silver (e.g. by elemental microanalysis or utilizing X-ray fluorescence), by obtaining the adsorbent surface area as described above and calculating.

The term "moisture content" as used herein in relation to the adsorbent means the water present in the particles of adsorbent according to measurement by Karl Fischer titration or by determining weight loss on ignition at 400° C. for 2-4 hours. The moisture content values presented herein are percentages by weight.

DETAILED DESCRIPTION

The alkyl carboxylates in the feed have the formula

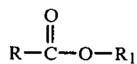

in which R is aliphatic chain which contains from 5 to 25 carbon atoms and is saturated (no double bonds in the aliphatic chain) or unsaturated (containing, for example, up to 5 double bonds in the aliphatic chain) and in which $R_1$ is an alkyl chain containing from 1 to 4 carbon atoms.

Alkyl carboxylates in the feed herein can be, for example, methyl caproate, methyl caprylate, methyl caprate, methyl laurate, ethyl laurate, methyl myristate, methyl myristoleate, methyl palmitate, ethyl palmitate, methyl palmitoleate; methyl stearate, ethyl stearate, propyl stearate, isopropyl stearate, butyl stearate, methyl oleate, ethyl oleate, propyl oleate, isopropyl oleate, butyl oleate, methyl linoleate, ethyl linoleate, methyl linolenate, ethyl linolenate, methyl eleostearate, methyl arachidate, methyl gadoleate, methyl arachidonate, methyl behenate, methyl erucate, ethyl erucate, methyl clupanodonate, methyl lignocerate, methyl nisinate and methyl shibate.

The feed into a one stage process or into the first stage of a multistage process is readily obtained, for example, by alcoholysis of naturally occurring triglyceride (e.g., by reaction of naturally occurring fats and oils with excess methanol in the presence of sodium methoxide). Very important feeds are obtained by methanolysis of cottonseed oil, soybean oil, regular safflower oil, high oleic safflower oil, sunflower oil and tallow. Feeds containing methyl esters are the most important commercially. One group of important feeds comprises by weight (total alkyl carboxylate basis) from 0% to about 60% methyl linolenate, from about 2% to about 80% methyl linoleate, from about 5% to about 75% methyl oleate, and from about 1% to about 35% methyl stearate; such feeds often also comprise by weight (total alkyl carboxylate basis) from about 5% to about 30% methyl palmitate.

It is desirable for the feed to be essentially free of impurities which can foul (i.e. deactivate) the adsorbent thereby causing loss of fractionating performance. Such impurities are not alkyl carboxylates as defined above and are materials which would be preferentially adsorbed and not desorbed thereby inactivating adsorption sites. When the feed is produced by alcoholysis of triglyceride, feed purity is readily obtained by clean-up of triglyceride prior to the alcoholysis reaction, and by reacting (and purifying, if necessary) to minimize free fatty acid level and other impurities. Clean-up of triglyceride to remove impurities such as gums, free fatty acids, color bodies, odor bodies, etc. is accomplished by numerous techniques known in the art, such as alkali refining, bleaching with Fuller's Earth or other active adsorbents, vacuum-steam stripping to remove odor bodies, etc.

In a one solvent process, the feed is usually introduced into the adsorbing unit without solvent and is dissolved in solvent already in the unit, introduced, for example, in a previous cycle to cause desorption. If desired, however, the feed in a one solvent process can be dissolved in solvent prior to introduction into the adsorbing unit or the feed can be raffinate or extract from a previous stage comprising alkyl carboxylate mixture dissolved in solvent. In a two solvent process, the feed is preferably dissolved in the solvent constituting the vehicle for adsorption prior to introduction into the adsorbing unit.

Turning now to the solvents useful herein for a one solvent process (where the same solvent composition performs the dual role of being the dissolving phase during adsorption and the vehicle for desorption), these are preferably characterized by $\delta$ ranging from about 7.0 to about 10.5, $\delta_D$ ranging from about 7.0 to about 9.0, $\delta_P$ ranging from about 0.2 to about 5.1 and $\delta_H$ ranging from about 0.3 to about 7.4. More preferred solvents for use in a one solvent process herein are characterized by $\delta$ ranging from about 7.4 to about 9.0, $\delta_D$ ranging from about 7.25 to about 8.0, $\delta_P$ ranging from about 0.5 to about 3.0 and $\delta_H$ ranging from about 0.7 to about 4.0.

One important group of solvents for a one solvent process includes those consisting essentially by volume of from 0% to about 90% $C_5$-$C_{10}$ saturated hydrocarbon (that is, saturated hydrocarbon with from 5 to 10 carbon atoms) and from 100% to about 10% carbonyl group containing compound selected from the group consisting of (a) ester having the formula

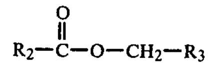

wherein $R_2$ is hydrogen or alkyl chain containing one or two carbon atoms and $R_3$ is hydrogen or alkyl chain containing one to three carbon atoms and (b) ketone having the formula

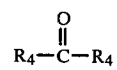

wherein each $R_4$ is the same or different and is alkyl chain containing 1 to 5 carbon atoms. Examples of suitable hydrocarbons are pentane, hexane, heptane, octane, nonane, decane, isopentane and cyclohexane. Examples of esters suitable for use in or as the solvent are methyl formate, methyl acetate, ethyl acetate, methyl propionate, propyl formate and butyl formate. Examples of ketones suitable for use in or as the solvent are acetone, methyl ethyl ketone, methyl isobutyl ketone and diethyl ketone.

Another important group of solvents for a one solvent process are dialkyl ethers containing 1 to 3 carbon atoms in each alkyl group and blends of these with the hydrocarbon, ester and ketone solvents set forth above. Specific examples of solvents within this group are diethyl ether and diisopropyl ether.

Yet another important group of solvents for a one solvent process are blends of $C_{1-3}$ alcohols (e.g. from about 5% to about 40% by volume alcohol) with the hydrocarbon, ester and ketone solvents set forth above. Specific examples of solvents within this group are blends of methanol or ethanol with hexane.

Very preferably, the solvent for a one solvent process comprises ethyl acetate with blending with hexane being utilized to weaken the solvent and blending with ethanol being utilized to strengthen the solvent.

In most continuous one solvent processes envisioned within the scope of the invention, the solvent is introduced into the process in a desorbing zone and sufficient solvent remains in the process to perform at a downstream location the dissolving function for adsorption.

The solvent to feed ratio for a one solvent process generally ranges on a volume basis from about 4:1 to about 100:1 and preferably ranges from about 5:1 to about 40:1.

We turn now to the solvents useful herein for a two solvent process (where different solvent compositions are used as the dissolving phase during adsorption and as the vehicle for desorption).

For a two solvent process herein, the solvents for use as the dissolving phase during adsorption, i.e., as the adsorption vehicle, are preferably characterized by $\delta$ ranging from about 7.3 to about 14.9, $\delta_D$ ranging from about 7.3 to about 9.0, $\delta_P$ ranging from 0 to about 5.7 and $\delta_H$ ranging from 0 to about 11.0. More preferred solvents for the adsorption vehicle for a two solvent process herein are characterized by $\delta$ ranging from about 7.3 to about 9.0, $\delta_D$ ranging from about 7.3 to about 8.0, $\delta_P$ ranging from 0 to about 2.7 and $\delta_H$ ranging from 0 to about 3.6. Very preferably, the solvent for the adsorption vehicle in a two solvent process herein is hexane or a blend consisting essentially of hexane and up to about 15% by volume ethyl acetate or diisopropyl ether.

For a two solvent process herein, the solvents for use as the vehicle for desorption, i.e., as the desorbent, are preferably characterized by $\delta$ ranging from about 7.4 to about 15.0 and at least 0.1 greater than the $\delta$ of the adsorption vehicle, $\delta_D$ ranging from about 7.3 to about 9.0, $\delta_P$ ranging from about 0.3 to about 6.0 and at least 0.3 greater than the $\delta_P$ of the adsorption vehicle, and $\delta_H$ ranging from about 0.5 to about 11.5 and at least 0.5 greater than the $\delta_H$ of the adsorption vehicle. More preferred solvents for the desorbent for a two solvent process herein are characterized by a $\delta$ ranging from about 7.4 to about 10.0, $\delta_D$ ranging from about 7.3 to about 8.0, $\delta_P$ ranging from about 0.5 to about 4.0, and $\delta_H$ ranging from about 0.5 to about 6.0 and having $\delta$, $\delta_P$ and $\delta_H$, respectively, greater than the $\delta$, $\delta_P$ and $\delta_H$ of the adsorption vehicle by at least the amounts stated above. Important desorbents for use in a two solvent process herein include: ethyl acetate; blends consisting essentially of ethyl acetate and up to about 80% by volume hexane; blends consisting essentially of ethyl acetate and up to about 25% by volume methanol or ethanol; and diisopropyl ether. Very preferably, the solvent for the desorbent in a two solvent process herein comprises ethyl acetate.

It is preferred both in a one solvent process herein and in a two solvent process herein to avoid use of halogenated hydrocarbon solvents as these shorten adsorbent life.

We turn now in detail to the adsorbent for use herein. It is defined the same regardless of whether it is used in a one solvent process or in a two solvent process.

The bonding of aluminate groups to surface-silicon atoms of the silica gel from which adsorbent herein is derived to provide the adsorbent herein characterized by aluminum atoms present essentially entirely in anionic moieties at the surface is indicated by the following chemical structure which is believed to represent anionic sites in such adsorbent:

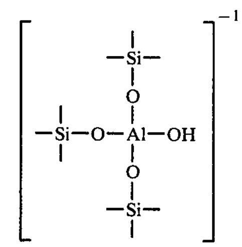

wherein the silicon atoms which are depicted are surface-silicon atoms. The cation substituents are associated with such anionic sites to provide electrostatic neutrality.

The characterization of the adsorbent herein in terms of surface area of the silica gel from which it is derived (silica gel starting material) is important to obtaining appropriate capacity. If silica gel starting material is utilized with a surface area less than the aforestated lower limit of about 100 square meters per gram, capacity becomes quite low. Preferably, the adsorbent herein is derived from silica gel having a surface area of at least about 300 square meters per gram. Silica gel starting materials are known with surface areas as high as 800 square meters per gram.

The characterization of the adsorbent herein in terms of ratio of surface-silicon atoms to aluminum atoms is important in relation to selectivity. The lower limit of about 3:1 is related to the chemical structure of the adsorbents herein; in such structure, aluminate moiety is associated with three silicon atoms. The upper limit of about 20:1 has been selected to provide sufficient adsorbing power to obtain selectivity in some fractionation envisioned. In most instances in important applications of this invention, the adsorbent preferably is characterized by a ratio of surface-silicon atoms to aluminum atoms ranging from about 3:1 to about 12:1.

We turn now to the cation substituents of the adsorbent.

The caton substituents capable of forming $\pi$ complexes are preferably selected from the group consisting of silver (in a valence state of 1), copper (in a valence state of 1), platinum (in a valence state of 2), palladium (in a valence state of 2) and combinations of these.

The cation substituents not capable of forming $\pi$ complexes are preferably selected from the group consisting of cation substituents from Groups IA and IIA of the Periodic Table and zinc cation substituents and combinations of these and very preferably are selected from the group consisting of sodium, potassium, barium, calcium, magnesium and zinc substituents and combinations of these.

Most preferably, the adsorbent has cation substituents selected from the group consisting of silver substituents in a valence state of one and sodium substituents and combinations of these.

Preferably, cation substituents such as hydrogen, which cause deterioration of the adsorbent structure (e.g. by stripping aluminum therefrom) or which foster significant polymerization, should be avoided or kept at a minimum.

Fractionations are envisioned herein utilizing adsorbent with no cation substituents capable of forming $\pi$ complexes (e.g. together with a weak solvent as the adsorption vehicle). Such adsorbent functions by a physical adsorption mechanism to preferentially adsorb more unsaturated alkyl carboxylate. Preferably, however, the adsorbent utilized has cation substituents capable of forming $\pi$ complexes as at least some of its cation substituents; these adsorbents function by a combination of physical adsorption and the type of chemical adsorption known as $\pi$ complexing to preferentially adsorb more unsaturated alkyl carboxylate.

Very preferably, the adsorbent has a level of silver substituents greater than about 0.05 millimoles/ 100 square meters of adsorbent surface area. The upper limit on silver is found in a fully silver exchanged adsorbent with a ratio of surface-silicon atoms to aluminum atoms of about 3:1 and is about 0.44 millimoles/100 square meters of adsorbent surface area. Most preferably, the adsorbent has a silver level ranging from about 0.10 millimoles/100 square meters of adsorbent surface area to about 0.35 millimoles/100 square meters of adsorbent surface area. Amount of silver is readily measured utilizing X-ray fluorescence or elemental microanalysis.

The ratio of surface-silicon atoms to aluminum atoms and the level of cation substituents capable of forming $\pi$ complexes interrelate, and the selection of these governs adsorbing power and therefore selectivity. These also have an effect on capacity.

The ratio of surface-silicon atoms to aluminum atoms selected sets the maximum amount of cation substituents capable of forming $\pi$ complexes that can be introduced. This is because the cation substituents are held by the negative charges associated with aluminum atoms in anionic moieties, with a monovalent cation substituent being held by the charge associated with a single aluminum atom and a divalent cation substituent being held by the charges associated with two aluminum atoms.

With the silica gel starting material surface area held constant, and with the level of cation substituents capable of forming $\pi$ complexes being held at the same percentage of exchange capacity, as the ratio of surface-silicon atoms to aluminum atoms is increased, the adsorbing power and capacity decreases. With the silica gel starting material surface area held constant and with the ratio of surface-silicon atoms to aluminum atoms held constant, increasing the level of cation substituents capable of forming $\pi$ complexes results in increasing adsorbing power and capacity. With the ratio of surface-silicon atoms to aluminum atoms held constant and the level of cation substituents capable of forming $\pi$ complexes held constant, using adsorbent derived from silica gel of increased surface area increases capacity.

The moisture content is important in the adsorbent because too much moisture causes the adsorbent to be oleophobic (water occupies pores of the adsorbent preventing feed from reaching solid surface of the adsorbent). The less the moisture content is, the greater the adsorbing power and capacity. The upper limit of about 10% by weight moisture content has been selected so that the adsorbent will perform with at least mediocre efficiency. Preferably, the moisture content in the adsorbent is less than about 4% by weight.

The adsorbents herein generally have particle sizes ranging from about 200 mesh to abut 20 mesh (U.S. Sieve Series). Use of a particle size less than about 200 mesh provides handling problems and can result in loss of adsorbent as a result of very small particles forming a stable suspension in solvent. Use of a particle size greater than about 20 mesh results in poor mass transfer. For a continuous process, particle sizes of about 80 mesh to about 30 mesh (U.S. Sieve Series) are preferred; using particle sizes larger than about 30 mesh reduces resolution and causes diffusion (mass transfer) limitations and using particle sizes less than about 80 mesh results in high pressure drops. Preferably, there is narrow particle size distribution within the aforestated ranges to provide good flow properties.

We turn now to the preparation of the adsorbent.

The silica gel starting material is selected on the basis of surface area and particle size. As indicated above, the surface area must be at least about 100 square meters per gram. The particle size must be at least about 200 mesh since the adsorbent has a particle size approximately the same as the particle size of the silica gel particles which are reacted to provide the adsorbent. Thus, microparticulate silica gels are unacceptable for use in producing the adsorbent herein. Silica gel starting materials including particles with a size greater than 20 mesh are readily made useful, for example, by sieving out larger particles if only some are present or by size-reducing and sieving if a substantial part of the particles is too large. Preferred silica gel starting materials are sold under the tradenames Silica Gel 100 and Geduran (both are manufactured by E. Merck and Company) and Grade 59 Silica Gel (manufactured by the Davison Chemical Division of W. R. Grace). Silica Gel 100 and Geduran are obtainable in particle size of 35–70 mesh. Grade 59 Silica Gel is obtainable in a particle size of 3–8 mesh and must undergo size reduction and sieving.

The aluminate ion can be furnished by using a water soluble aluminate or a source thereof (in other words, the aluminate can be formed in situ). Preferred water-soluble aluminate reactants are sodium aluminate and potassium aluminate. Aluminate is suitably formed in situ, for example, by reacting cationic aluminum (e.g., from aluminum nitrate) with sodium hydroxide, or by reacting aluminum metal with sodium hydroxide.

The reaction involving aluminate ion and silica gel is suitably carried out as follows: Firstly, an aqueous solution of aluminate ion (or precursors thereof) is contacted with selected silica gel. The amount of aluminate ion is selected to provide the desired ratio of surface-silicon atoms to aluminum atoms. Reaction temperatures range, for example, from about 15° C. to about 100° C. and reaction times range, for example, from about 1 to about 48 hours. In one useful process, reaction is carried out at room temperature. In another useful process, boiling water (100° C.) is used as the reaction medium. Reaction is carried out to obtain the desired surface alumination. After the surface alumination is completed, it is desirable to wash the product, e.g. with distilled water, to remove excess aluminum salts.

Lam et al, cited above, suggest the following reaction equation:

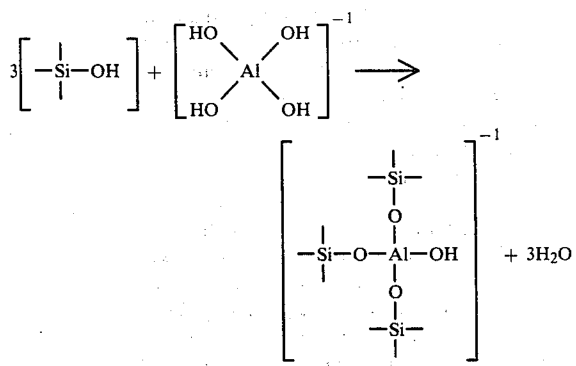

If the surface alumination reaction described above does not provide the proper cation substituents in the selected level, a cation exchange is carried out.

The cation exchange to provide a selected level of cation substituents capable of forming $\pi$ complexes is readily carried out by contacting the aluminated material with a sufficient amount of cation that is desired to be introduced. When it is desired to introduce silver substituents to provide cation substituents capable of forming $\pi$ complexes, the exchange is carried out in aqueous medium. Suitable sources of silver include silver nitrate which is preferred and silver fluoride, silver chlorate and silver perchlorate. When the level of cation desired to be introduced is substantially less than 100% of exchange capacity, reaction is preferably carried out in a stirred tank and a slight excess of cation (preferably 105–115% of stoichiometric) is desirably used. When the level of cation desired to be introduced approaches 100% of exchange capacity, reaction is preferably carried out in a packed column and a large excess (preferably 200% of stoichiometric) is used. Unreacted cation is readily washed from the product.

The moisture content is readily adjusted with conventional drying methods. For example, drying is readily carried out using vacuum or an oven (e.g. a forced draft oven). Drying is carried out to obtain the desired moisture level, e.g., by drying at a temperature of 100° C.–110° C. for 15–20 hours.

The particle size of the adsorbent is preferably adjusted by adjusting the particle size of the silica gel starting material, for example, by sieving (screening) to obtain a narrow size distribution of particles within the aforedescribed range and by size reducing when such is appropriate. Particle size of adsorbent is readily controlled in this manner because particle size of the aluminated reaction product is essentially the same as that of the silica gel reactant. Less preferably, sieving or size-reduction can be carried out on aluminated reaction product or even on reaction product subsequent to cation treatment.

Turning now to the instant fractionation process, the selection of solvent(s), ratio of surface-silicon atoms to aluminum atoms in the adsorbent and level of cation substituents capable of forming $\pi$ complexes are interrelated and depend on the separation desired to be obtained. The lower the ratio of surface-silicon atoms to aluminum atoms in the adsorbent is, the greater the adsorbing power is. The higher the level of cation substituents capable of forming $\pi$ complexes is, the greater the adsorbing power and the greater the resistance to desorption. The lower the solubility parameter and solubility parameter polar and hydrogen bonding components of the solvent utilized as the dissolving phase during adsorption are, the more adsorbing power a particular adsorbent is able to exert. The higher the solubility parameter and the solubility parameter polar and hydrogen bonding components of the solvent utilized as the vehicle for desorption are, the more the desorbing power. The higher the degree of unsaturation of the fraction desired to be separated is, the higher the solubility parameter and solubility parameter polar and hydrogen bonding components of the solvent that can be used for adsorbing and that is required for desorbing and the higher the ratio of surface-silicon atoms to aluminum atoms and the lower the level of cation substituents capable of forming $\pi$ complexes in the adsorbent that can be used for adsorbing and which will allow desorbing.

When a particular adsorbent has been selected, the solvent used during adsorbing should have a solubility parameter and solubility parameter components sufficiently low to obtain selectivity, and the solvent used for desorbing should have a solubility parameter and solubility parameter components sufficiently high to obtain desorption.

When a particular solvent or particular solvents has (have) been selected, an adsorbent is selected with a ratio of surface-silicon atoms to aluminum atoms sufficiently low and a level of cation substituents capable of forming $\pi$ complexes sufficiently high to provide desired selectivity during adsorption and with a ratio of surface-silicon atoms to aluminum atoms sufficiently high and a level of cation substituents capable of forming $\pi$ complexes sufficiently low to allow desorpton of all or desired portion of adsorbed alkyl carboxylate during the desorbing step.

We turn now to the conditions of temperature and pressure for the instant fractionation process. The temperatures utilized during adsorbing and during desorbing can be the same and generally range from about 20° to 150° C. A preferred temperature range to be used when the feed is a mixture of alkyl carboxylates having fatty carboxylic acid moieties with aliphatic chains having from 12 to 20 carbon atoms, is about 50° to about 80° C. Lower temperatures within the above described broad range are preferably utilized when the solvent comprises ketone. The pressures utilized during adsorbing and desorbing can be the same and generally are those pressures encountered in packed bed processing, e.g., ranging from atmospheric (14.7 psia) to about 500 psia. For a simulated moving bed process as described hereafter, the pressures utilized preferably range from about 30 psia to about 120 psia or are as prescribed by the desired flow rate.

For a batch process, sufficient residence time should be provided to obtain appropriate yields and purities, usually 15 minutes to 20 hours. The rates for continuous processing are a function of the size of the equipment, the resolving ability of the adsorbent-solvent pair, and the desired yield and purity.

The fractionation process herein as described above provides a "raffinate" and an "extract". The raffinate contains fraction which is enriched in content of alkyl carboxylate of lesser degree of unsaturation. It comprises alkyl carboxylate which was weakly attracted by the adsorbent, dissolved in solvent. The extract contains fraction enriched in content of alkyl carboxylate of higher degree of unsaturation. It comprises alkyl carboxylate which was more strongly attracted by the adsorbent, dissolved in solvent. The fractions can be recovered from the raffinate and from the extract by conventional separation processes such as by stripping solvent with heat and vacuum.

We turn now to apparatus for a one solvent process herein and its operation.

For batch processing, the one solvent process herein is readily carried out in equipment conventionally used for adsorptions carried out batchwise. For example, such processing can be carried out utilizing a column containing adsorbent and alternately (a) introducing feed dissolved in solvent to obtain selective adsorption and (b) introducing solvent to obtain desorption of adsorbed fraction.

For continuous processing, the one solvent process herein is readily carried out in conventional continuous adsorbing apparatus and is preferably carried out by means of a simulated moving bed unit operation. A simulated moving bed unit operation and apparatus for such useful herein is described in Broughton et al U.S. Pat. No. 2,985,589.

For a simulated moving bed embodiment of this invention, preferred apparatus includes: (a) at least four columns connected in series, each containing a bed of adsorbent; (b)liquid access lines communicating with an inlet line to the first column, with an outlet line from the last column, and with the connecting lines between successive columns; (c) a recirculation loop including a variable speed pump, to provide communication between the outlet line from the last column and the inlet line to the first column; and (d) means to regulate what flows in or out of each liquid access line.

Such preferred simulated moving bed apparatus is operated so that liquid flow is in one direction and so that countercurrent flow of adsorbent is simulated by manipulation of what goes into and out of the liquid access lines. In one embodiment, the apparatus is operated so that four functional zones are in operation. The first of the functional zones is usually referred to as the adsorption zone. This zone is downstream of a feed inflow and upstream of a raffinate outlfow. In the adsorption zone, there is a net and selective adsorption of alkyl carboxylate of higher degree of unsaturation and a net desorption of solvent and of alkyl carboxylate of lesser degree of unsaturation. The second of the functional zones is usually referred to as the purification zone. It is downstream of an extract outflow and upstream of the feed inflow and just upstream of the adsorption zone. In the purification zone, alkyl carboxylate of higher degree of unsaturation which has previously been desorbed is preferentially adsorbed and there is a net desorption of solvent and of alkyl carboxylate of lesser degree of unsaturation. The third of the functional zones is referred to as the desorption zone. It is downstream of a solvent inflow and upstream of extract outflow and just upstream of the purification zone. In the desorption zone, there is a net desorption of alkyl carboxylate of higher degree of unsaturation and a net adsorption of solvent. The fourth functional zone is usually referred to as the buffer zone. It is downstream of the raffinate outflow and upstream of the solvent inflow and just upstream of the desorption zone. In the buffer zone, alkyl carboxylate of lesser degree of unsaturation is adsorbed and solvent is desorbed. The various liquid access lines are utilized to provide the feed inflow between the purification and adsorption zones, the raffinate outflow between the adsorption and buffer zones, solvent inflow between the buffer and desorption zones and extract outflow between the desorption and purification zones. The liquid flow is manipulated at predetermined time periods and the speed of the pump in the recirculation loop is varied concurrent with such manipulation so that the inlet points (for feed and solvent) and the outlet points (for raffinate and extract) are moved one position in the direction of liquid flow (in a downstream direction) thereby moving the aforedescribed zones in the direction of liquid flow and simulating countercurrent flow of adsorbent.

In another embodiment of simulated moving bed operation, a plurality of successive desorption zones is utilized (in place of a single desorption zone) with solvent being introduced at the upstream end of each desorption zone and extract being taken off at the downstream end of each desorption zone. It may be advantageous to use different solvent inlet temperatures and/or different solvents for different desorption zones.

In another embodiment of simulated moving bed processing, raffinate is taken off at a plurality of locations along the adsorption zone.

Less preferred continuous simulated moving bed apparatus than described above is the same as the apparatus described above except that the recirculation loop is omitted. The buffer zone can also be omitted.

In the operation of the above described simulated moving bed processes, the relative number of columns in each zone to optimize a process can be selected based on selectivities and resolution revealed by pulse testing coupled with capacity and purity requirements. A factor in selecting the number of columns in the adsorption zone is the percentage of the feed to be absorbed. The purity of the extract and raffinate streams is a function of the number of columns in the adsorption zone. The longer the adsorption zone is (the more columns in it), that is, the further removed the feed inlet is from the raffinate outlet, the purer the raffinate is.

In the operation of the above described simulated moving bed processes, the time interval between manipulations of liquid flow should be sufficient to allow a substantial proportion of alkyl carboxylate of higher degree of unsaturation to stay in the adsorption zone and a substantial proportion of alkyl carboxylate of lesser degree of unsaturation to leave.

We turn now to apparatus for the two solvent process herein and its operation.

Such two solvent process is preferably carried out using a column loaded with adsorbent. The feed and the solvent constituting the adsorption vehicle are run through the column until a desired amount of feed is adsorbed. Then, the desorbing solvent is run through the column to cause desorption of adsorbed material.

Such two solvent process is less preferably carried out, for example, in a batch mixing tank containing the adsorbent. The feed together with solvent constituting the adsorption vehicle is added into the tank. Then mixing is carried out until a desired amount of adsorption occurs. Then liquid is drained. Then desorbing solvent is added and mixing is carried out until the desired amount of desorption occurs. Then solvent containing the desorbed alkyl carboxylate is drained.

We turn now in more detail to the multistage process referred to generally above.

Multistage processing can involve the following. The feedstock to be separated is processed in a first stage to obtain first extract containing fraction enriched (compared to the feedstock) in content of alkyl carboxylate of higher degree of unsaturation and first raffinate containing fraction enriched (compared to the feedstock) in content of alkyl carboxylate of lesser degree of unsaturation and depleted (compared to the feedstock) in content of alkyl carboxylate of higher degree of unsaturation. The first raffinate or first extract, preferably the alkyl carboxylate fraction obtained by essentially completely removing solvent from first raffinate or first extract, is processed in the second stage to obtain second extract containing fraction enriched in content of alkyl carboxylate of higher degree of unsaturation (compared to the feed to the second stage) and second raffinate enriched (compared to the feed to the second stage) in content of alkyl carboxylate of lesser degree of unsaturation and depleted (compared to feed to the second stage) in content of alkyl carboxylate of higher degree of unsaturation. To the extent succeeding stages are used, each succeeding stage has as its feed raffinate or extract from the proceding stage, preferably alkyl carboxylate fraction obtained by essentially completely removing solvent from such.

We turn now to some important applications of the instant process.

One application is a process in which the alkyl carboxylate feed mixture comprises a mixture of methyl ester of polyunsaturated fatty acid, methyl ester of monounsaturated fatty acid and methyl ester of saturated fatty acid and in which alkyl carboxylate of higher degree of unsaturation comprises methyl ester of polyunsaturated fatty acid. Feeds for this application can be derived, for example, from regular safflower oil, high oleic safflower oil, soybean oil or sunflower oil. Processing of the feeds derived from regular safflower oil and sunflower oil gives a product containing a very high percentage of methyl linoleate.

Another application is a process in which the alkyl carboxylate feed mixture comprises a mixture of methyl ester of monounsaturated fatty acid and methyl ester of saturated fatty acid and in which alkyl carboxylate of higher degree of unsaturation comprises methyl ester of monounsaturated acid. Feeds for this application can be fraction obtained, for example, from raffinate from a first of a two stage process in which the feed to the first stage is derived from high oleic safflower oil or soybean oil or sunflower oil. This gives product containing a very high percentage of methyl oleate.

Still another application is a process in which the alkyl carboxylate feed mixture comprises a mixture of methyl ester of triunsaturated fatty acid and methyl ester of diunsaturated fatty acid and in which the alkyl carboxylate of higher degree of unsaturation is methyl ester of triunsaturated fatty acid. A feed for this application can be derived, e.g., from soybean oil.

We turn now to advantages of the process herein.

Significant advantages result from the chemical composition and structure of the adsorbent herein. Firstly, such adsorbent is made from materials which are readily commercially available in large amounts. Secondly, flexibility in adsorbent composition is readily provided in that silica gels with different surface areas are readily available and in that a predetermined ratio of surface-silicon atoms to aluminum atoms is readily obtained. Thirdly, level of cations capable of forming $\pi$ complexes can be readily regulated by selecting the ratio of surface-silicon atoms to aluminum atoms. Fourthly, any cations capable of forming $\pi$ complexes are situated at the surface of the adsorbent where such are available to provide adsorbing power thereby providing efficient usage of such cations (e.g. silver).

Furthermore, the process herein is characterized by a long adsorbent life cycle. Firstly, there is no problem of cations capable of forming $\pi$ complexes being leached from the adsorbent as there is with silver nitrate treated silica gel adsorbents. This is because the cations are attached in the adsorbent herein by electrostatic interaction. Secondly, there is no fouling of the adsorbent with impurities. Thirdly, the adsorbent has physical strength such that it does not break down into smaller pieces.

Moreover, processing is carried out without any significant amount of polymerization so that there is no problem of disposing of polymer by-product.

Furthermore, the process herein is carried out without the adsorbent handling and loss problems which can be associated with use of microparticulate particle size adsorbents.

Furthermore, the adsorbent herein has a high capacity for adsorbing alkyl carboxylates compared to resin adsorbents. This means higher throughput rates or smaller equipment size and reduction in usage of active cations (e.g. silver).

Furthermore the adsorbent herein is advantageous over resin adsorbents and crystalline zeolite adsorbents from the standpoint of flexibility and is advantageous over resin adsorbents in being inorganic in nature.

Furthermore, with the adsorbent herein, contrary to the case with crystalline zeolite adsorbents, the same equipment and adsorbent are appropriately used to separate alkyl carboxylate mixtures and triglyceride mixtures.

The invention is illustrated in the following specific examples.

In Examples I–III below, "pulse tests" are run to determine the quality of separation that can be obtained in one solvent processing with selected adsorbents and solvents. The apparatus consists of a column having a length of 120 cm. and an inside diameter of 1 cm. and having inlet and outlet ports at its opposite ends. The adsorbent is dispersed in solvent and then introduced into the column. The column is packed with about 100 cc. of adsorbent on a wet packed basis. The column is in a temperature controlled environment. A constant flow pump is used to pump liquid through the column at a predetermined flow rate. In the conducting of the tests, the adsorbent is allowed to come to equilibrium with the particular solvent and feed by passing a mixture of the solvent and feed through the column for a predetermined period of time. The adsorbent is then flushed with solvent until a 5 milliliter fraction contains a negligible amount of feed. At this time, a pulse of feeding containing a known amount of docosane tracer is injected, via a sample coil, into the solvent inflow. The pulse of feed pulse tracer is thereby caused to flow through the column with components first being adsorbed by the adsorbent and then caused to be desorbed by the solvent. Equal volume effluent samples are collected, and alkyl carboxylate therefrom is analyzed by gas chromatography. From these analyses, elution concentration curves for tracer and alkyl carboxylate components are obtained (concentration in milligrams per milliliter is plotted on the y axis and elution volume in milliliters is plotted on the x axis). The distance from time zero (the time when the pulse of feed plus tracer is introduced) to the peak of a curve is the elution volume. The difference between the elution volume for an alkyl carboxylate component and the elution volume for the tracer is the retention volume of that alkyl carboxylate component. The relative selectivity of one ester component over another (when the selected adsorbent and solvent are utilized) is the ratio of their respective retention volumes.

In Example IV, pilot plant test apparatus (sometimes referred to as a demonstration unit) is utilized. The apparatus is operated according to the continuous simulated moving bed unit operation mentioned above to carry out a one solvent process. The apparatus comprises fourteen columns which are connected in series in a loop to permit the process liquid to flow in one direction. Each column has a length of 24 inches and an inside diameter of 9/10 of an inch and is loaded with about 237 cc. of adsorbent (wet packed basis). Each column is equipped with two four-position valves (top and bottom) connected to four inlet and four outlet conduits. When a valve is closed, liquid flows only toward the column downstream of the valve. By selecting between the eight open positions (four at top and four at bottom), feed can be caused to be introduced to the system (e.g. position 1), solvent can be caused to be introduced to the system (e.g. position 2), a raffinate stream can be removed from the system (e.g. position 3) or an extract stream can be removed from the system (e.g. position 4). Backflow check positions are located in each of the bottom valves. These are used to isolate zones of the system from backflow; i.e., isolate the high pressure inlet (solvent) from the lower pressure outlet. Operation is as follows: At any time, the apparatus constitutes a single stage. It is operated with three working zones (adsorption, purification and desorption). One backflow control valve is always in closed position to eliminate backflow between the solvent inlet and the low pressure outlet. No recirculation is used. The fourteen columns are apportioned between the adsorption, purification and desorption zones with a selected number of columns in series comprising each zone. Feed is introduced into the first column of the adsorption zone and is dissolved in solvent and is contacted with adsorbent. As liquid flows downstream through the adsorption zone, alkyl carboxylate component(s) of higher degree of unsaturation is (are) selectively adsorbed leaving raffinate enriched in alkyl carboxylate of lower degree of unsaturation. In the purification zone, non-adsorbed components are forced from the adsorbent and are thus forced downstream toward the feed point. The extract is removed at the inlet to the purification zone and is enriched in adsorbed components. The solvent is added at the inlet to the desorption zone and causes desorption of adsorbed component(s) from the adsorbent for removal downstream at the extract point. At selected intervals a controller advances the flow pattern (into and out of columns) one column (in other words, the controller manipulates valves so that raffinate outflow, feed inflow, extract outflow and solvent inflow points each advance one step, that is, to the next liquid access point in the direction of liquid flow) to "step forward" to keep pace with the liquid flow. Fourteen "steps" constitute a cycle. The "step time" is chosen such as to allow the non-adsorbed components to advance faster than the feed point and reach the raffinate point. The adsorbed alkyl carboxylate moves slower than the feed point and falls behind to the extract point.

In Example V below, a test is run to demonstrate selection of solvents for a two solvent process once a particular adsorbent has been selected. The apparatus utilized is the same as that utilized in the runs of Examples I–III, and as in Examples I–III the column is packed with about 100 cc. of adsorbent (wet packed basis). The following procedure is utilized. A plurality of solvent is utilized successively, each being of progressively increasing desorbed power. The initial solvent is pumped through the column at 5 ml/minute with the column temperature being 50° C. 2.0 gms of feed (0.1 gram docosane tracer and 1.9 gms alkyl carboxylate mixture) is dissolved in 10 ml. of the initial solvent. Flow through the column is stopped, and the 10 ml. of initial solvent with feed dissolved therein is injected into the column entrance. Flow of initial solvent is then restarted and effluent sample collection is begun. After approximately two column volumes of the initial solvent is pumped into the column, the solvent is changed and approximately two column volumes of the second solvent is pumped into the column. The solvent is successively changed after two column volumes of a solvent is pumped until all the solvents being tested have been pumped into the column. Eluant samples are collected, and the alkyl carboxylate therefrom is analyzed by gas chromatography.

We turn now to the Examples I–V which are generally described above.

EXAMPLE I

This example involves pulse testing to determine solvent and adsorbent combinations useful for continuous simulated moving bed processing for various fractionations of safflower methyl ester feedstock (containing, by weight, 8.0% methyl palmitate, 2.5% methyl stearate, 13.0% methyl oleate, and 76.5% methyl linoleate).

Six runs are carried out.

In each run, the pulse consists of 0.5 ml. solvent, 0.1 gm docosane tracer and 0.4 gm of the above described safflower methyl ester feedstock.

In Run 1 and in Run 2, the adsorbent has the following characteristics: It is derived from silica gel having a surface area of 470 square meters per gram. It is also characterized by a ratio of surface-silicon atoms to aluminum atoms of 4.97:1, a moisture content less than 2% by weight, and a particle size of 35-70 mesh (U.S. Sieve Series). It contains 0.33 millimoles of silver (in the form of cation substituents in a valence state of 1) per 100 square meters of adsorbent surface area. The silver substituents make up 97.6% of the exchangeable cations. The remainder of the exchangeable cations are sodium substituents. The surface area of the first adsorbent is 366 square meters per gram.

The adsorbent for Runs 1 and 2 is made as follows: Grade 59 Silica Gel (3-8 mesh U.S. Sieve Series) is gently crushed, and a fraction with particle size range of 35-70 mesh is recovered. 1000 grams of such fraction and 2 liters of distilled water are charged into a 5.0 liter, 3-neck, fluted flask fitted with a mechanical stirrer, a pH electrode, and an addition funnel. The mixture is agitated to form a homogeneous slurry. The pH of the slurry is adjusted to 9.5 with 10% aqueous sodium hydroxide solution. Then a freshly prepared solution of sodium aluminate (112.2 gm) in distilled water (2.0 liters) is added. The slurry is stirred 10 hours at room temperature (about 20° C.). Then stirring is stopped and the mixture is allowed to stand overnight. The resulting product is poured into a glass chromatographic column and washed free of unreacted aluminate with distilled water (1-2 ml per minute). Then, the material in the column is treated with a solution of silver nitrate (a two-fold molar equivalent of silver based on the aluminate reagent) in distilled water. Flow rate of the silver exchange solution is about 0.5 ml/minute. The solid is then washed with distilled water to remove excess silver nitrate, suction filtered to remove bulk water, and dried in a forced draft oven (105°-110° C.) overnight.

In Run 3 and in Run 4, the adsorbent has the following characteristics: It is derived from silica gel having a surface area of 346 square meters per gram. It is also characterized by a ratio of surface-silicon atoms to aluminum atoms of 5.06:1, a moisture content less than 2% by weight, and a particle size of 35-70 mesh (U.S. Sieve Series). It contains 0.25 millimoles of silver (in the form of cation substituents in a valence state of 1) per 100 square meters of adsorbent surface area. The silver substituents make up 94.3% of the exchangeable cations. The remainder of the exchangeable cations are sodium substituents. The surface areas of the final adsorbent is 339 square meters per gram.

The adsorbent for Runs 3 and 4 is made the same as that for Runs 1 and 2 except that Silica Gel 100 is used instead of Grade 59 Silica Gel and except that alumination is carried out for 4 hours at 80° C.

In Run 5 and in Run 6, the adsorbent has the following characteristics: It is derived from silica gel having a surface area of 346 square meters per gram. It is also characterized by a ratio of surface-silicon atoms to aluminum atoms of 11.4:1, a moisture content less than 2% by weight, and a particle size of 35-70 mesh (U.S. Sieve Series). It contains 0.13 millimoles of silver (in the form of cation substituents in a valence state of 1) per 100 $m^2$ of adsorbent surface area. The silver substituents make up 78.3% of the exchangeable cations. The remainder of exchangeable cations are sodium substituents. The surface area of the final adsorbent is 245 square meters per gram.

The adsorbent for Runs 5 and 6 is made the same as that for Runs 3 and 4 except 43.4 gms of sodium aluminate is used and except for the silvering procedure. For silvering, the product of the reaction of silica gel and sodium aluminate is transferred to a reaction vessel, and a solution of silver nitrate (82.8 grams) in distilled water is added. This mixture is stirred for 10-20 minutes and left standing overnight at room temperature. The exchange liquor is then removed by suction filtration and the solid is washed until wash effluent contains no detectable silver ion. Dewatering and drying is carried out the same as for the adsorbent for Runs 1 and 2.

The solvent for Runs 1 and 3 consists by volume of 60% hexane and 40% ethyl acetate (for this solvent blend: $\delta=7.66$; $\delta_D=7.46$; $\delta_P=1.04$; $\delta_H=1.40$). The solvent for Runs 2, 4 and 6 consists by volume of 100% ethyl acetate ($\delta=8.85$, $\delta_D=7.70$, $\delta_P=2.60$, $\delta_H=3.50$). The solvent for Run 5 consists by volume of 40% hexane and 60% ethyl acetate (for this solvent blend: $\delta=7.85$; $\delta_D=7.54$; $\delta_P=1.56$; $\delta_H=2.10$).

Each of the runs is carried out at 50° C.

In each run: Solvent is pumped continously through the column at a rate of 5 ml. per minute. At time zero, a sample pulse as described above is introduced by means of the sample coil into the solvent flow. The equal volume samples that are collected are each 5 ml.

In Run 1, retention volumes are obtained as follows: for methyl palmitate, 0; for methyl stearate, 0; for methyl oleate, 30 ml; for methyl linoleate, 125 ml.

In Run 1, relative selectivities are obtained as follows: for methyl oleate/methyl stearate, ∞; for methyl linoleate/methyl stearate, ∞; for methyl linoleate/methyl oleate, 4.17.

In Run 2, retention volumes are obtained as follows: for methyl palmitate, 0; for methyl stearate, 0; for methyl oleate, 20 ml; for methyl linoleate, 85 ml.

In Run 2, relative selectivities are obtained as follows: for methyl oleate/methyl stearate, ∞; for methyl linoleate/methyl stearate, ∞; for methyl linoleate/methyl oleate, 4.25.

In Run 3, retention volumes are obtained as follows: for methyl palmitate, 10 ml.; for methyl stearate, 10 ml.; for methyl oleate, 30 ml.; for methyl linoleate, 110 ml.

In Run 3, relative selectivities are obtained as follows: for methyl palmitate/methyl stearate, 1.00; for methyl oleate/methyl stearate, 3.00; for methyl linoleate/methyl stearate, 11.00; for methyl linoleate/methyl oleate, 3.67.

In Run 4, retention volumes are obtained as follows: for methyl palmitate, 5 ml.; for methyl stearate, 5 ml.; for methyl oleate, 20 ml.; for methyl linoleate, 75 ml.

In Run 4, relative selectivities are obtained as follows: for methyl palmitate/methyl stearate, 1.00; for methyl oleate/methyl stearate, 4.00; for methyl linoleate/methyl stearate, 15.00; for methyl linoleate/methyl oleate, 3.75.

In Run 5, retention volumes are obtained as follows: for methyl palmitate, 5 ml.; for methyl stearate, 5 ml.; for methyl oleate, 10 ml.; for methyl linoleate, 20 ml.

In Run 5, relative selectivities are obtained as follows: for methyl palmitate/methyl stearate, 1.00; for methyl oleate/methyl stearate, 2.00; for methyl linoleate/methyl stearate, 4.00; for methyl linoleate/methyl oleate, 2.00.

In Run 6, retention volumes are obtained as follows: for methyl palmitate, 0; for methyl stearate; 0; for methyl oleate, 5 ml.; for methyl linoleate, 10 ml.

In Run 6, relative selectivities are obtained as follows: for methyl oleate/methyl stearate, ∞; for methyl linoleate/methyl stearate, ∞; for methyl linoleate/methyl oleate, 2.00

The above runs indicate that to obtain one fraction enriched in methyl linoleate and other fraction enriched in the other components in simulated moving bed processing, the adsorbent best utilized out of those tested is the adsorbent of Runs 1 and 2 and the solvent can be either the solvent of Run 1 or the solvent of Run 2. The above runs indicate that to obtain one fraction enriched in unsaturates and other fraction enriched in saturates, the adsorbent best utilized out of those tested is the adsorbent of Runs 1 and 2 and the solvent can be either the solvent of Run 1 or the solvent of Run 2. The different splits are accomplished by apportioning the columns in the simulated moving bed processing differently amongst the four zones. To provide a fraction enriched in methyl linoleate but not in methyl oleate, fewer columns are used in the adsorption zone than are used to provide a fraction enriched in both methyl oleate and methyl palmitate.

EXAMPLE II

This example involves pulse testing to determine solvent and adsorbent combination useful for fractionation of soybean methyl ester feedstock (that is, methyl ester mixture derived from soybean oil and containing, by weight, 12.5% methyl palmitate, 3.8% methyl stearate, 23.1% methyl oleate, 53.4% methyl linoleate, and 7.2% methyl linolenate).

Two runs are carried out.

In each run, the pulse consists of 0.5 ml. solvent, 0.1 gm docosane tracer and 0.4 gm of the above described soybean methyl ester feedstock.

In both the runs, the adsorbent has the following characteristics: It is derived from silica gel having a surface area of 346 square meters per gram. It is also characterized by a ratio of surface-silicon atoms to aluminum atoms of 6.4:1, a moisture content less than 2% by weight, and a particle size of 35-70 mesh (U.S. Sieve Series). It contains sodium substituents as all of its cation substituents.

The adsorbent is made as follows: Silica Gel 100 (35-70 mesh U.S. Sieve Series) is utilized. 1000 grams of the silica gel and 2 liters of distilled water are charged into a 5.0 liter, 3-neck, fluted flask fitted with a mechanical stirrer, a pH electrode, and an addition funnel. The mixture is agitated to form a homogeneous slurry. The pH of the slurry is adjusted to 9.5 with 10% aqueous sodium hydroxide solution. Then a freshly prepared solution of sodium aluminate (108.6 gm) in distilled water (2.0 liters) is added. The slurry is stirred 10 hours at room temperature (about 20° C.). Then stirring is stopped and the mixture is allowed to stand overnight. The resulting product is poured into a glass chromatographic column and washed free of unreacted aluminate with distilled water (1-2 ml per minute). Washing is continued until the pH of the effluent is about 9.0. The solid is suction filtered to remove bulk water and then dried in a forced-draft oven (105°-110° C.) overnight.

The solvent for Run 1 consists by volume of 99% hexane and 1% ethyl acetate (for this solvent blend: $\delta=7.30$; $\delta_D=7.30$; $\delta_P=0.03$; $\delta_H=0.04$). The solvent for Run 2 consists by volume of 97% hexane and 3% ethyl acetate (for this solvent blend: $\delta=7.31$; $\delta_D=7.31$; $\delta_P=0.08$; $\delta_H=0.11$).

Each of the runs is carried out at 50° C.

In each run: Solvent is pumped continuously through the column at a rate of 5 ml. per minute. At time zero, a sample pulse as described above is introduced by means of the sample coil into the solvent flow. The equal volume samples that are collected are each 5 ml.

In Run 1, retention volumes are obtained as follows: for methyl palmitate, 135 ml; for methyl stearate, 135 ml; for methyl oleate, 145 ml; for methyl linoleate, 170 ml; for methyl linolenate, 185 ml.

In Run 1, relative selectivities are obtained as follows: for methyl palmitate/methyl stearate, 1.00; for methyl oleate/methyl stearate, 1.07; for methyl linoleate/methyl stearate, 1.26; for methyl linolenate/methyl stearate, 1.37; for methyl linoleate/methyl oleate 1.17; for methyl linolenate/methyl oleate, 1.28; and for methyl linolenate/methyl linoleate, 1.09.

In Run 2, retention volumes are obtained as follows: for methyl palmitate, 55 ml; for methyl stearate, 55 ml; for methyl oleate, 55 ml; for methyl linoleate, 60 ml; for methyl linolenate, 65 ml.

In Run 2, relative selectivities are obtained as follows: for methyl palmitate/methyl stearate, 1.00; for methyl oleate/methyl stearate, 1.00; for methyl linoleate/methyl stearate, 1.09; for methyl linolenate/methyl stearate, 1.18; for methyl linoleate/methyl oleate, 1.09; for methyl linolenate/methyl oleate, 1.18; for methyl linolenate/methyl linoleate, 1.08.

These runs indicate that fraction enriched in methyl linolenate can be obtained using the adsorbent of Example II and the solvent consisting by volume of 99% hexane and 1% ethyl acetate.

EXAMPLE III

This example involves pulse testing to determine solvent and silvered adsorbent combination useful to fractionate soybean methyl ester feedstock to produce one fraction enriched in methyl linolenate and depleted in other components and other fraction depleted in methyl linolenate and enriched in other components.

One run is carried out.

The pulse is the same as that used in Example II.

The adsorbent has the following characteristics: It is derived from silica gel having a surface area of 346 square meters per gram. It is also characterized by a ratio of surface-silicon atoms to aluminum atoms of 6.4:1, a moisture content less than 2% by weight, and a particle size of 35-50 mesh (U.S. Sieve Series). It contains 0.27 millimoles of silver (in the form of cation substituents in a valence state of 1) per 100 square meters of adsorbent surface area. The silver substituents make up 67.6% of the exchangeable cations. The remainder of the exchangeable cations are sodium substituents. The surface area of the final adsorbent is 233 square meters per gram.

The adsorbent is made up the same as the adsorbent for Runs 5 and 6 of Example I except for the following differences. Silica Gel 100 is screened to provide a 35-50 mesh fraction for reaction. 108.6 gms of sodium aluminate is used in the surface aluminating reaction. 156 gms of silver nitrate is used in the silvering procedure.

The solvent consists by volume of 30% ethyl acetate and 70% hexane (for this solvent blend: $\delta=7.53$, $\delta_D=7.42$, $\delta_P=0.78$, $\delta_H=1.05$).

The run is carried out at 50° C.

In the run, solvent is pumped continuously through the column at a rate of 5 ml per minute. At time zero, a sample pulse as described above is introduced by means of the sample coil into the solvent flow. The equal volume samples that are collected are each 5 ml.

In the run, retention volumes and selectivities are obtained indicating fractionation on the basis of unsaturation wherein the ester of triunsaturated fatty acid is the alkyl carboxylate of higher degree of unsaturation. In other words the run indicates the adsorbent—solvent combination tested is advantageously used to obtain one fraction enriched in methyl linolenate and other fraction enriched in the other alkyl carboxylates.

EXAMPLE IV

This example illustrates separation of a mixture of methyl oleate and methyl linoleate to provide one fraction enriched in methyl oleate and a second fraction enriched in methyl linoleate. The run is carried out in the demonstration unit as described above.

The feed composition consists by weight of 25% methyl oleate and 75% methyl linoleate.

The adsorbent is the same as that used in Example III.

The solvent consists by volume of 20% ethyl acetate and 80% hexane. for this solvent blend: $\delta=7.43$, $\delta_D=7.38$, $\delta_P=0.52$, and $\delta_H=0.70$.

The controller and the valves of the demonstration unit are set so that the adsorption zone includes 4 columns, the purification zone includes 4 columns and the desorption zone includes 6 columns.

The step time (the interval at which the flow pattern is advanced one column) is 7 minutes. The feed rate is 1.25 ml. per minute. The solvent introduction rate is 42.63 ml. per minute. The extract flow rate is 13.88 ml. per minute. The raffinate flow rate is 30.00 ml. per minute.

The temperature of operation is 50° C.

The raffinate obtained consists (total fatty acid ester basis) by weight of 97.80% methyl oleate and 2.20% methyl linoleate. The extract obtained consists (total fatty acid ester basis) by weight of 0.70% methyl oleate and 99.30% methyl linoleate.

The above indicates separation according to degree of unsaturation.

The adsorbent particle size used presents no significant handling or loss (because of suspension in solvent) problems. There is no significant leaching of silver. There is no fouling of adsorbent with impurities. No polymers are detected in the product. The same equipment and adsorbent is readily used for separating triglyceride mixtures.

Where in the run of Example IV, the process is operated using 16 columns and so that the adsorption zone includes 5 columns, the purification zone includes 5 columns and the desorption zone includes 6 columns, the raffinate (total fatty acid ester basis) consists of 100% methyl oleate and the extract stream (total fatty acid ester basis) consists of 100% methyl linoleate.

When in the run of Example IV, the feed instead consists of the safflower methyl ester feedstock of Example I, there is separation to provide one fraction enriched in methyl ester of polyunsaturated fatty acid and other fraction enriched in methyl ester of saturated fatty acid and methyl ester of monounsaturated fatty acid.

When in the run of Example IV, the feed consists instead by weight of (a) 25% ethyl oleate and 75% ethyl linoleate or (b) 25% propyl oleate and 75% propyl linoleate or (c) 25% butyl oleate and 75% butyl linoleate, fractionation according to degree of unsaturation is obtained.

When in the run of Example IV, an equivalent amount of copper or platinum or palladium is substituted for the silver substituents of the adsorbent, results are obtained indicating attainment of fractionation according to degree of unsaturation.

When in the run of Example IV, an equivalent amount of potassium, barium, calcium, magnesium or zinc substituents is substituted for the sodium substituents of the adsorbent, results are obtained indicating fractionation according to degree of unsaturation.

When a solvent consisting by volume of 15% acetone and 85% hexane (for this solvent blend: $\delta=7.40$, $\delta_D=7.35$, $\delta_P=0.77$, $\delta_H=0.51$) is substituted in Example IV for the hexane/ethyl acetate solvent, fractionation according to degree of unsaturation is obtained.

When a solvent consisting by volume of 65% hexane and 35% diethyl ether (for this solvent blend: $\delta=7.30$, $\delta_D=7.23$, $\delta_P=0.49$, $\delta_H=0.88$) is substituted in Example IV for the hexane/ethyl acetate solvent, fractionation according to degree of unsaturation is obtained.

When a solvent consisting by volume of 10% ethanol and 90% hexane (for this solvent blend: $\delta=7.41$, $\delta_D=7.34$, $\delta_P=0.43$, $\delta_H=0.95$) is substituted in Example IV for the hexane/ethyl acetate solvent, fractionation according to degree of unsaturation is obtained.

When Amberlyst XN1010 (a macroreticular strong acid cation exchange resin sold by Rohm & Haas) with an equivalent amount of silver to that used in Example IV is substituted for the adsorbent in Example IV, the fractionation obtained is significantly less complete.

When Zeolite X or Zeolite Y or silvered Zeolite X or silvered Zeolite Y is substituted as the adsorbent in Example IV, the same equipment and adsorbent is not appropriately used for separation of methyl esters and triglycerides.

EXAMPLE V

The alkyl carboxylate mixture for fractionation is derived from soybean oil and consists by weight of 12.5% methyl palmitate, 3.8% methyl stearate, 23.1% methyl oleate, 53.4% methyl linoleate, and 7.2% methyl linolenate.

The adsorbent is from the same batch as that used in Runs 1 and 2 of Example I.

The solvent used first consists by volume of 100% hexane ($\delta=7.30$, $\delta_D=7.30$, $\delta_P=0$, $\delta_H=0$); this solvent is denoted Solvent I below. The solvent used second consists by volume of 90% hexane and 10% ethyl acetate (for this solvent blend: $\delta=7.35$, $\delta_D=7.34$, $\delta_P=0.26$, and $\delta_H=0.35$); this solvent is denoted Solvent II below. The solvent used third consists by volume of 50% hexane and 50% ethyl acetate (for this solvent blend: $\delta=7.81$, $\delta_D=7.50$, $\delta_P=1.30$, $\delta_H=1.75$); this solvent is denoted Solvent III below. The solvent used fourth consists by volume of 100% ethyl acetate ($\delta=8.85$, $\delta_D=7.70$, $\delta_P=2.60$, $\delta_H=3.50$); this solvent is denoted Solvent IV below. The solvent used fifth consists by volume of 100% methanol ($\delta=14.5$, $\delta_D=7.4$, $\delta_P=6.0$, $\delta_H=10.9$); this solvent is denoted Solvent V below.

The test is carried out at 50° C.

Solvent I is pumped through the "pulse test" column described above at 5.0 ml/minute. With flow stopped, a "pulse" containing 2.0 grams (95% soybean methyl ester described above and 5% $C_{22}$ linear hydrocarbon tracer) dissolved in 10 ml of Solvent I is injected into the column entrance. Flow of Solvent I is then restarted, and eluant sample collection begins. After approximately two column volumes of Solvent I are pumped, the solvent is changed to Solvent II, then to Solvent III, etc., with approximately two column volumes of each solvent being pumped in succession after the above described feed injection. Eluant samples are collected and analyzed.

The table below presents data for this run. In the table: 16=0 stands for methyl palmitate, 18=0 stands for methyl stearate, 18=1 stands for methyl oleate, 18=2 stands for methyl linoleate, and 18=3 stands for methyl linolenate. The values given opposite each solvent represent the alkyl carboxylate composition eluted with that particular solvent.

TABLE

SEPARATION OF SOYBEAN METHYL ESTERS IN A TWO SOLVENT PROCESS

| Solvent | %16 = 0 | %18 = 0 | %18 = 1 | %18 = 2 | %18 = 3 |
|---|---|---|---|---|---|
| I | 73.15 | 26.85 | — | — | — |
| II | — | — | 33.32 | 66.68 | — |
| III | — | — | — | 25.80 | 74.2 |
| IV | — | — | — | — | — |
| V | — | — | — | — | — |

The above data indicates that with the selected adsorbent: Saturates are best separated from unsaturates using hexane as the adsorption vehicle and 50/50 hexane/ethyl acetate as the desorbent. To provide fraction free of methyl linolenate, hexane can be the adsorbent and 90/10 hexane/ethyl acetate the desorbent. To provide fraction enriched in methyl linolenate and depleted in other components, the adsorbing solvent should be 90/10 hexane/ethyl acetate and the desorbent should be 50/50 hexane/ethyl acetate. To separate polyunsaturates, the adsorbing solvent should contain by volume between 0 and 10% hexane (with the remainder ethyl acetate) and the desorbent should be 50/50 hexane/ethyl acetate. Other solvents and blends can be substituted provided there is similarity of solubility parameters and solubility parameter components.

While the foregoing describes certain preferred embodiments of the invention, modifications will be readily apparent to those skilled in the art. Thus, the scope of the invention is intended to be defined by the following claims.

What is claimed is:

1. A process for separating an alkyl carboxylate mixture according to degree of unsaturation, said process comprising the steps of (a) contacting a solution of said mixture in solvent with surface aluminated silica gel adsorbent to selectively adsorb alkyl carboxylate of higher degree of unsaturation and to leave in solution in solvent a fraction of said mixture enriched in content of alkyl carboxylate of lesser degree of unsaturation, (b) removing solution of fraction enriched in content of alkyl carboxylate of lesser degree of unsaturation from contact with adsorbent which has selectively adsorbed alkyl carboxylate of higher degree of unsaturation, (c) contacting adsorbent which has selectively adsorbed alkyl carboxylate of higher degree of unsaturation with solvent to cause desorption of adsorbed alkyl carboxylate and provide solution in solvent of fraction enriched in content of alkyl carboxylate of higher degree of unsaturation, (d) removing solution of fraction enriched in content of alkyl carboxylate of higher degree of unsaturation from contact with adsorbent;

the alkyl carboxylate in said mixture having the formula

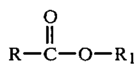

in which R is aliphatic chain which contains from 5 to 25 carbon atoms and in which $R_1$ is alkyl chain containing from 1 to 4 carbon atoms; the solvent in step (a) and the solvent in step (c) having the same composition or different compositions and being characterized by a solubility parameter (on a 25° C. basis) ranging from about 7.0 to about 15.0, a solubility parameter dispersion component (on a 25° C. basis) ranging from about 7.0 to about 9.0, a solubility parameter polar component (on a 25° C. basis) ranging from 0 to about 6.0 and a solubility parameter hydrogen bonding component (on a 25° C. basis) ranging from 0 to about 11.5; said adsorbent being derived from silica gel having a surface area of at least about 100 square meters per gram; said adsorbent being further characterized by a ratio of surface-silicon atoms to aluminum atoms ranging from about 3:1 to about 20:1, a moisture content less than about 10% by weight, and a particle size ranging from about 200 mesh to about 20 mesh; said adsorbent having cation substituents selected from the group consisting of cation substituents capable of forming $\pi$ complexes and cation substituents not capable of forming $\pi$ complexes and combinations of these; the solvent in step (a) and the solvent in step (c) and the ratio of surface-silicon atoms to aluminum atoms in the adsorbent and the level of cation substituents capable of forming $\pi$ complexes being selected to provide selectivity in step (a) and desorption in step (c).

2. A process as recited in claim 1 in which the cation substituents capable of forming $\pi$ complexes are selected from the group consisting of silver, copper, platinum and palladium cation substituents and combinations of these, and in which the cation substituents not capable of forming $\pi$ complexes are selected from the group consisting of cation substituents from Group IA of the Periodic Table, cation substituents from Group IIA of the Periodic Table, zinc cation substituents and combinations of these.

3. A process as recited in claim 2, in which the adsorbent has cation substituents selected from the group consisting of silver substituents in a valence state of one and sodium substituents and combinations of these.

4. A process as recited in claim 3, in which the adsorbent is characterized by a level of silver substituents greater than about 0.05 millimoles/100 square meters of adsorbent surface area.

5. A process as recited in claim 4, in which the solvent in each step has the same composition and is characterized by a solubility parameter (on a 25° C. basis) ranging from about 7.0 to about 10.5, a solubility parameter dispersion component (on a 25° C. basis) ranging from about 7.0 to about 9.0, a solubility parameter polar component (on a 25° C. basis) ranging from about 0.2 to about 5.1, and a solubility parameter hydrogen bonding component (on a 25° C. basis) ranging from about 0.3 to about 7.4.

6. A process as recited in claim 5, in which the solvent is characterized by a solubility parameter (on a 25° C. basis) ranging from about 7.4 to about 9.0, a solubility parameter dispersion component (on a 25° C. basis) ranging from about 7.25 to about 8.0, a solubility parameter polar component (on a 25° C. basis) ranging from about 0.5 to about 3.0 and a solubility parameter hydrogen bonding component (on a 25° C. basis) ranging from about 0.7 to about 4.0.

7. A process as recited in claim 5 in which said solvent comprises ethyl acetate.

8. A process as recited in claim 5, in which said adsorbent is derived from silica gel having a surface area of at least about 300 square meters per gram and is further characterized by a ratio of surface-silicon atoms to aluminum atoms ranging from about 3:1 to about 12:1, a silver level ranging from about 0.10 millimoles/100 square meters of adsorbent surface area to about 0.35 millimoles/100 square meters of adsorbent surface area, and a moisture content less than about 4% by weight.

9. A process as recited in claim 8, which is carried out by a continuous simulated moving bed technique.

10. A process as recited in claim 9, in which the alkyl carboxylate mixture is a mixture of methyl esters.

11. A process as recited in claim 4, in which the solvent in step (a), the adsorption vehicle, has a different composition from the solvent in step (c), the desorbent.

12. A process as recited in claim 11, in which the adsorption vehicle is characterized by a solubility parameter (on a 25° C. basis) ranging from about 7.3 to about 14.9, a solubility parameter dispersion component (on a 25° C. basis) ranging from about 7.3 to about 9.0, a solubility parameter polar component (on a 25° C. basis) ranging from 0 to about 5.7, and a solubility parameter hydrogen bonding component (on a 25° C.

basis) ranging from 0 to about 11.0, in which the desorbent is characterized by a solubility parameter (on a 25° C. basis) ranging from about 7.4 to about 15.0 and at least 0.1 greater than that of the adsorption vehicle, a solubility parameter dispersion component (on a 25° C. basis) ranging from about 7.3 to about 9.0, a solubility parameter polar component (on a 25° C. basis) ranging from about 0.3 to about 6.0 and at least 0.3 greater than that of the adsorption vehicle, and a solubility parameter hydrogen bonding component (on a 25° C. basis) ranging from about 0.5 to about 11.5 and at least 0.5 greater than that of the adsorption vehicle.

13. A process as recited in claim 12, in which the adsorption vehicle is characterized by a solubility parameter (on a 25° C. basis) ranging from about 7.3 to about 9.0, a solubility parameter dispersion component (on a 25° C. basis) ranging from about 7.3 to about 8.0, a solubility parameter polar component (on a 25° C. basis) ranging from 0 to about 2.7, and a solubility parameter hydrogen bonding component (on a 25° C. basis) ranging from 0 to about 3.6; and in which the desorbent is characterized by a solubility parameter (on a 25° C. basis) ranging from about 7.4 to about 10.0, a solubility parameter dispersion component (on a 25° C. basis) ranging from about 7.3 to about 8.0, a solubility parameter polar component (on a 25° C. basis) ranging from about 0.5 to about 4.0 and a solubility parameter hydrogen bonding component (on a 25° C. basis) ranging from about 0.5 to about 6.0.

14. A process as recited in claim 13, in which the adsorption vehicle comprises hexane and in which the desorbent comprises ethyl acetate.

15. A process as recited in claim 12, in which said adsorbent is derived from silica gel having a surface area of at least about 300 square meters per gram and is further characterized by a ratio of surface-silicon atoms to aluminum atoms ranging from about 3:1 to about 12:1, a silver level ranging from about 0.10 millimoles/100 square meters of adsorbent surface area to about 0.35 millimoles/100 square meters of adsorbent surface area, and a moisture content less than about 4% by weight.

16. A process as recited in claim 4, in which the alkyl carboxylate mixture comprises a mixture of methyl ester of polyunsaturated fatty acid, methyl ester of monounsaturated fatty acid and methyl ester of saturated fatty acid and in which alkyl carboxylate of higher degree of unsaturation comprises methyl ester of polyunsaturated fatty acid.

17. A process as recited in claim 4, in which the alkyl carboxylate mixture comprises a mixture of methyl ester of monounsaturated fatty acid and methyl ester of saturated fatty acid and in which alkyl carboxylate of higher degree of unsaturation comprises methyl ester of monounsaturated fatty acid.

18. A process as recited in claim 4, in which the alkyl carboxylate mixture comprises a mixture of methyl ester of triunsaturated fatty acid and methyl ester of diunsaturated fatty acid and in which the alkyl carboxylate of higher degree of unsaturation is methyl ester of triunsaturated fatty acid.

* * * * *